(12) United States Patent
Sun et al.

(10) Patent No.: US 10,912,518 B2
(45) Date of Patent: Feb. 9, 2021

(54) FUSING SENSOR SIGNALS INDICATING A SAME PHYSIOLOGICAL PARAMETER BASED ON QUALITY INDICES OF EACH SIGNAL

(71) Applicant: Shenzhen Mindray Bio-Medical Electronics Co., Ltd., Shenzhen (CN)

(72) Inventors: Ze-Hui Sun, Shenzhen (CN); Jiao Yu, Shenzhen (CN); Jian-Wei Su, Shenzhen (CN); Jing-Ming Yang, Shenzhen (CN); Chao-Cheng Xie, Shenzhen (CN); Wen-Yu Ye, Shenzhen (CN); Jian Cen, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 1101 days.

(21) Appl. No.: 15/068,662

(22) Filed: Mar. 14, 2016

(65) Prior Publication Data

US 2016/0192887 A1     Jul. 7, 2016

Related U.S. Application Data

(63) Continuation of application No. PCT/CN2014/074131, filed on Mar. 26, 2014.

(30) Foreign Application Priority Data

Sep. 13, 2013   (CN) .......................... 2013 1 0419867

(51) Int. Cl.
  *A61B 5/00*    (2006.01)
  *G06K 9/00*    (2006.01)
  *G06K 9/62*    (2006.01)

(52) U.S. Cl.
  CPC .......... *A61B 5/7221* (2013.01); *G06K 9/0051* (2013.01); *G06K 9/00536* (2013.01); *G06K 9/6293* (2013.01)

(58) Field of Classification Search
  None
  See application file for complete search history.

(56) References Cited

U.S. PATENT DOCUMENTS 5,626,140 A  *  5/1997  Feldman .............. G06K 9/6293
                                          600/483

FOREIGN PATENT DOCUMENTS

| CN | 101683260 | 3/2010 |
| CN | 102283642 | 12/2011 |
| CN | 102316792 | 1/2012 |

OTHER PUBLICATIONS

Li, Qiao, and Gari D. Clifford. "Signal quality and data fusion for false alarm reduction in the intensive care unit." Journal of electrocardiology 45.6 (2012): 596-603.*
Li, Qiao, Roger G. Mark, and Gari D. Clifford. "Robust heart rate estimation from multiple asynchronous noisy sources using signal quality indices and a Kalman filter." Physiological measurement 29.1 (2007): 15.*

* cited by examiner

*Primary Examiner* — G Steven Vanni
(74) *Attorney, Agent, or Firm* — Kory D. Christensen

(57) ABSTRACT

A computer-implemented method for a monitoring device being executed by a processor of the monitoring device comprises acquiring at least two kinds of physiological signals via a sensor of the monitoring device, obtaining a signal quality index of each of the at least two kinds of physiological signals by the processor of the monitoring device, providing a homologous physiological parameter value corresponding to each of the at least two kinds of physiological signals by the processor of the monitoring device, and fusing the homologous physiological parameter values based on the signal quality index of each of the at least two kinds of physiological signals and providing a fused value of the homologous physiological parameter values by the processor of the monitoring device. The disclosed physiological parameter processing method avoids disadvantages caused by relying on a single physiological signal.

14 Claims, 4 Drawing Sheets

FUSING SENSOR SIGNALS INDICATING A SAME PHYSIOLOGICAL PARAMETER BASED ON QUALITY INDICES OF EACH SIGNAL

CROSS-REFERENCE TO RELATED APPLICATIONS

This application claims all benefits accruing under 35 U.S.C. § 119 from China Patent Application No. 201310419867.6, filed on Sep. 13, 2013 in the China Intellectual Property Office, the content of which is hereby incorporated by reference. This application is a continuation under 35 U.S.C. § 120 of international patent application No. PCT/CN2014/074131, filed on Mar. 26, 2014.

BACKGROUND

1. Field

The present invention relates to medical devices, and more particularly to a physiological parameters processing method and system and monitoring device of the same.

2. Background

There are many applications of obtaining physiological parameter by processing signals of vital signs of humans. However, the signals of these readings often suffer interference from noise and artifacts resulting in errors. Taking a monitoring device as an example, improper estimations of arrhythmia could lead to false alarms, which reduces the confidence of patients and medical staff. More severely, if medical staff lose confidence in alarms from the monitoring device then a critical situation may get ignored, which greatly weakens the effectiveness of monitoring.

SUMMARY

The present disclosure provides a physiological parameter processing method and system and a monitoring device.

A computer-implemented method for a monitoring device, wherein the monitoring device comprises a sensor, a processor and a storage device that stores one or more programs, includes:

acquiring at least two kinds of physiological signals via the sensor;

obtaining a signal quality index of each of the at least two kinds of physiological signals by the processor;

providing a homologous physiological parameter value corresponding to each of the at least two kinds of physiological signals by the processor; and fusing the homologous physiological parameter values based on the signal quality index of each of the at least two kinds of physiological signals and providing a fused value of the homologous physiological parameter values by the processor.

A physiological parameter processing system of a monitoring device, which comprises a sensor, a processor and a storage device that stores one or more programs, includes:

a receiving module, acquiring at least two kinds of physiological signals via the sensor;

a signal quality index module, obtaining a signal quality index of each of the at least two kinds of physiological signals by the processor;

an obtaining module, obtaining a homologous physiological parameter value corresponding to each of the at least two kinds of physiological signals by the processor; and a fusion module, fusing the homologous physiological parameter values based on the signal quality index of each of the at least two kinds of physiological signals and providing a fused value of the homologous physiological parameter values by the processor.

A monitoring device comprises a sensor, at least one processor, and a storage device that stores one or more programs, when executed by the at least one processor, cause the at least one processor to:

acquire at least two kinds of physiological signals;

obtain a signal quality index of each of the at least two kinds of physiological signals;

provide a homologous physiological parameter value corresponding to each of the at least two kinds of physiological signals; and fuse the homologous physiological parameter values based on the signal quality index of each of the at least two kinds of physiological signals and provide a fused value of the homologous physiological parameter values.

The physiological parameter processing method and system and the monitoring device acquire at least two kinds of physiological signals, obtain their respective signal quality indexes and fuse the at least two physiological parameter values of a same kind got by the physiological signals based on the signal quality indexes. This avoids the disadvantage of obtaining a parameter only based on a single physiological signal. When a physiological signal is interfered with, the disclosed method utilizes other signals to improve the signal processing.

BRIEF DESCRIPTION OF THE DRAWINGS

The present invention is illustrated by way of embodiments and accompanying drawings.

DETAILED DESCRIPTION

The following description provides embodiments with specific details to one skilled in the art for a better understanding of the present disclosure. However, it should be understood that the present disclosure could be practiced even without these details. In some embodiments, to avoid unnecessarily obscuring the descriptions of the embodiments, well-known structures and functions are not illustrated or not described in detail. In the specification and claims of the present disclosure, terms such as "including"

and "comprising" should be comprehended as an inclusive meaning instead of an exclusive or exhaustive meaning, i.e., it means "including but not limited to" unless specifically described otherwise in the context. In this detailed description section, singular or plural terms include both the plural and singular meanings as well.

Traditional physiological parameter processing methods, such as the classic filter, machine self-learning, Kalman filtering, and transform domain analysis, are studied and developed based on one single physiological signal, and intend to improve the estimation of physiological parameters when the single physiological signal is interfered with by noise. However, these methods do not give an advanced solution to the problem of the noise interference, and some algorithms are complicated and require too many resources to implement. In addition, there are also methods that select likely or reasonable physiological signals from a plurality of physiological data sources, but they do not give an advanced solution to the false alarms or missing alarms problem caused by noise interference either and are only practicable in a limited scope.

Figure 1:
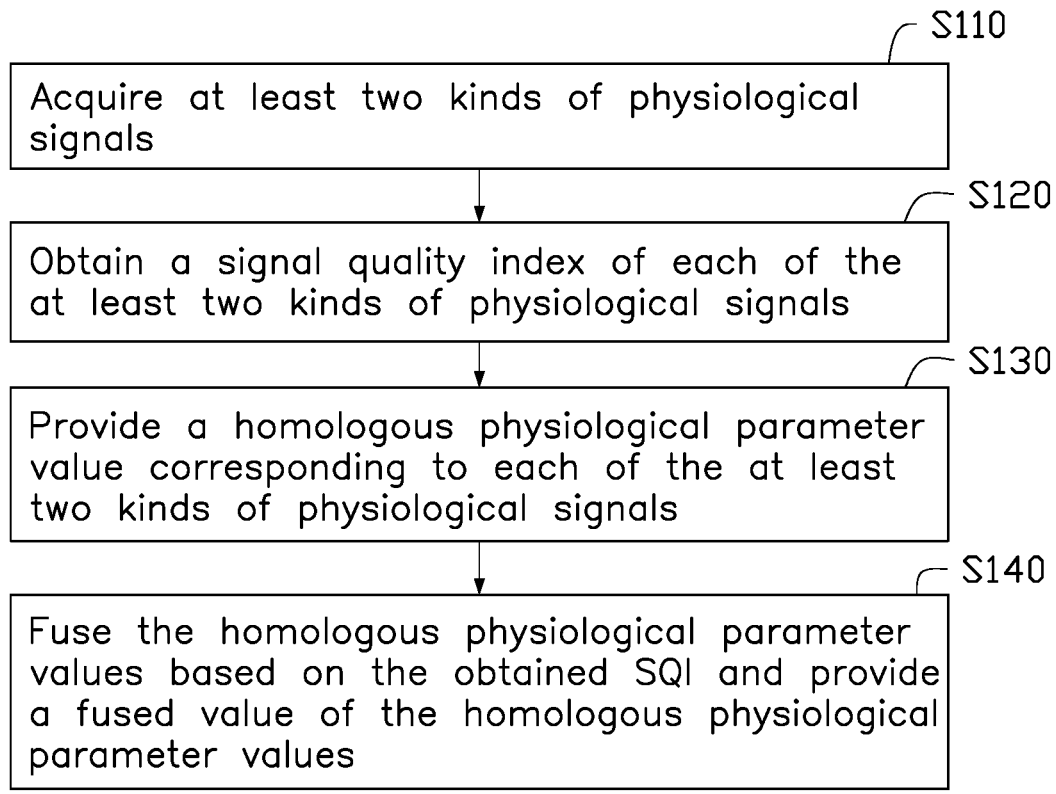
FIG. 1 is a flowchart illustrating a physiological parameter processing method.

FIG. 1 shows an embodiment of a physiological parameter processing method for a monitoring device which includes a sensor, a processor and a storage device, including the following steps.

At Step S110, at least two kinds of physiological signals are acquired by the sensor of the monitoring device. A physiological signal could be an electrocardiography signal (ECG signal), an invasive blood pressure signal (IBP signal), or a blood oxygen signal (SPO2 signal). The phrase, "at least two kinds of physiological signals," may include only two kinds of physiological signals or more than two kinds of physiological signals. For example the number of kinds of the physiological signal could be two, three, four, or more. The acquired physiological signal could be either an original signal collected via the sensor or a signal processed by a filter or other processing methods.

At Step S120, the processor of the monitoring device obtains a signal quality index (SQI, Signal Quality Index) of each physiological signal by analyzing each of the at least two kinds of physiological signals. The SQI is an evaluation of the quality of the physiological signal. The SQI could be calculated by various approaches, such as an individual calculation or a comprehensive calculation. The SQI could also be corrected based on some pre-determinations. Approaches to obtain the SQI will be described in detail.

At Step S130, a homologous physiological parameter value is provided corresponding to each of the at least two kinds of physiological signal by processing each of the at least two kinds of physiological signals by the monitoring device. For example, a physiological parameter value may be obtained by IBP algorithm analysis, SPO2 algorithm analysis, and ECG algorithm analysis. For example, diastolic pressure, systolic pressure, mean blood pressure and pulse rate could be obtain by processing an IBP signal, pulse rate and blood oxygen saturation degree could be obtained by processing an SPO2 signal, and heart rate and arrhythmia could be obtained by processing an ECG signal. Related to these physiological parameter values, the homologous physiological parameter values could be ECG heart rate (HR), IBP pulse rate ($PR_{Ibp}$) and SPO2 pulse rate (PRspo2). The homologous physiological parameter values indicates the same physiological status but are obtained from different signal sources.

At Step S140, a processor of the monitoring device fuses the homologous physiological parameter values based on the signal quality index of each of the at least two kinds of physiological signals and provides a fused value of the homologous physiological parameter values. The fused value could be obtained by applying a weighted average method to fuse the homologous physiological parameter values obtained from the at least two kinds of physiological signals. A weighting of the physiological parameter value obtained from each physiological signal is determined by the SQI of each physiological signal. An SQI indicating a good quality of the physiological signal has a higher weighting of the physiological parameter value than that of an indicated poor quality. The fusing process could also proceed by other statistical methods, such as a Kalman filtering method, to fuse the at least two homologous physiological parameter values.

The aforementioned physiological parameter processing method acquires at least two kinds of physiological signals via the sensor of a monitoring device and obtains their respective SQIs and fuses, by the processor of the monitoring device, the at least two homologous physiological parameter values based on the SQIs. Thus the method can avoid the disadvantage of obtaining physiological parameters only based on one single physiological signal. A single physiological signal could be improved by use of the physiological parameter of the other physiological signal when the single physiological signal is interfered with.

It should be noted that the purpose of the aforementioned physiological parameter processing method is not to obtain a diagnostic result or health status directly. The disclosed method cannot process physiological signals to obtain diagnostic results directly, but could fuse processed physiological parameter values, based on the SQI, to avoid false alarms. That is, the aforementioned physiological parameter processing method could adjust existing physiological parameter values. The obtained results could include intermediate parameters which do not in themselves indicate diagnostic results or health status. Thus the aforementioned method does not belong to diagnosis or treatment methods.

Figure 2:
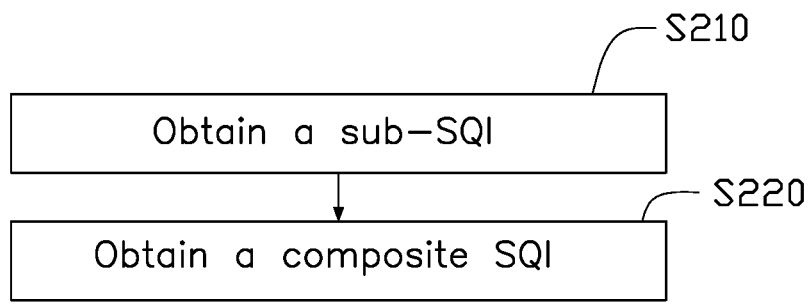
FIG. 2 is a flowchart illustrating an embodiment of the analysis of a physiological signal to obtain a signal quality index.

As shown in FIG. 2, in step S120, the step of obtaining the SQI of each physiological signal by analyzing each of the at least two kinds of physiological signals via a processor of a monitoring device further includes the following specific steps.

At Step S210, the sub-SQI characterizing features or status of each individual physiological signal are obtained. Taking an ECG signal as an example, the sub-SQI could be one or more types of kSQI, bSQI, sSQI, hSQI, and bslSQI. The kSQI represents a type of ventricular fibrillation (VF) and is more likely to be a noiseless QRS complex when kSQI has a higher value, generally a value of 7. The sSQI represents the ratio of the valid signal to the whole signal and is more likely to be a noiseless QRS complex when sSQI has a higher value, generally a value of 0.6. The bslSQI represents the degree of baseline drift; a higher value of bslSQI indicates a smaller baseline drift which has less effect on the algorithm. It is therefore based on the effect which it has on the algorithm. The bslSQI could be divided into two levels or even more than two levels depending on the specific algorithm. The hSQI represents the magnitude of the high frequency noise; a higher value of hSQI indicates a lower high frequency noise which has less effect on the algorithm, therefore its effect on the algorithm hSQI could be divided into four levels or even more than four levels depending on the specific algorithm. The bSQI represents the magnitude of the composite noise; a smaller value of bSQI indicates a lower high frequency noise which has less effect on the algorithm, therefore its effect on the algorithm bSQI could be divided into fewer levels depending on the specific algorithm.

The kSQI could effectively represent the characteristic of the VF type, which is defined as:

$$kSQI = \frac{E\{(x-\mu_x)^4\}}{\sigma^4}$$

wherein, x is a discrete signal or a continuous series of signals, $\mu_x$ and $\sigma$ are the mean and the standard deviations of the discrete signal x or of the continuous series of signal x respectively, and E is a mathematical expectation operator.

The bSQI describes the percentage of matched beats by two QRS detection algorithms, representing the magnitude of noise, which is defined as follows:

$$bSQI = \frac{N_{matched}(k, w)}{N_{all}(k, w)} * 100$$

wherein, k is the QRS complex under analysis, w is a sliding analysis window (the width could be 10 seconds) centered in the analyzed QRS complex (k) with ½ window width at the left and right sides; $N_{matched}$ is the number of matches of the QRS complex in w detected by two different QRS detection algorithms (that is, any two types of QRS complex detection algorithms, for example DF algorithms and LT algorithms), and $N_{all}$ is the sum of the number of QRS complexes in w respectively detected by the two QRS detection algorithms. For example, in $N_{all}=N_1+N_2-N_{matched}$, $N_1$ is the number of QRS complexes in w detected by QRS detection algorithm 1, and $N_2$ is the number of QRS complexes in w detected by QRS detection algorithm 2. The matching of QRS complexes is based on the recommended standard from the Association for the Advancement of Medical Instrumentation (AAMI). When the labeled positions of QRS complexes detected by two algorithms are within 150 ms, these two QRS complexes are determined as being a single QRS complex. The meaning of bSQI is that the applied two algorithms could both label the QRS complexes correctly and a high bSQI value is obtained when the signal quality is good. The DF algorithm and LT algorithm could make different and misdetermined determinations, and a low bSQI value is obtained when the interference happens. Thus, the bSQI could characterize the magnitude of noise. The calculation of the bSQI could also be applied to IBP and SPO2 while the matched time window should be determined according to their own criteria for each example, e.g., 150 ms for the aforementioned ECG and 200 ms for IBP and SPO2.

The sSQI represents the ratio of the valid signals to the whole signals, showing the percentage of the power spectral density (PSD) of QRS complex in the total PSD, as shown below:

$$sSQI = 100 * \frac{\int_{f=thd1}^{f=thd2} PSD(k, w)\, df}{\int_{f=thd1}^{f=thd3} PSD(k, w)\, df}$$

Taking ECG as an example, most of the energy of QRS complex is focused on a frequency band centralized in 10 Hz with an approximate width of 10 Hz and the upper limit of the total energy is about 50 Hz. In the equation thd1 could thus be selected as 5 Hz, thd2 could be selected as 14 Hz, and thd3 could be selected as 50 Hz. According to the spectral analysis of the ECG signal, the energy of QRS complexes are focused on a frequency band centralized in 10 Hz with an approximate width of 10 Hz. The percentage of the PSD of the spectrum in the total PSD could be utilized as a reference index to determine the quality of the ECG signal. The calculation of sSQI could also be applied to IBP and SPO2, but the bandwidth for the calculation should be determined according to the own criteria of each, for example, calculating the ratio of 5-14 Hz to 5-5 Hz for the aforementioned ECG, while calculating the ratio of 0.2-12 Hz to 0.2-60 Hz for IBP and SPO2.

The hSQI is an index representing the magnitude of high frequency noise, calculated by:

$$hSQI=10*min(QRS_{i\_amplitude}/hf\_noise_i)$$

wherein $QRS_{i\_amplitude}$ refers to the amplitude of the currently detected QRS complex, $hf\_noise_i$ is the mean value of the previous sum of 0.28 s–0.05 s before QRS complex, sum(i)=|hf(i)|+|hf(i−1)|+ . . . +|hf(i−5)|, wherein the hf is a value obtained by filtering ECG signal through a high pass filter: hf(i)=χ(i)−χ(i−1)+χ(i−2) wherein χ refers to the original waveform of ECG or the processed data of the waveform of ECG The bslSQI is an index representing the degree of baseline drift, calculated by:

$$bslSQI=10*min(QRS_{i\_amplitude}/baseline_{i\_amplitude})$$

wherein, $QRS_{i\_amplitude}$ is the difference between the maximum and minimum values in the range of QRS complex (R−0.07 s~R+0.08 s); and $baseline_{i\_amplitude}$ is the difference between the maximum and minimum values of the window phase for the baseline determination (R−1 s~R+1 s).

The sub-SQI is not limited to the aforementioned five types. One classification or characterization of a current signal could be the sub-SQI, such as the SQI representing energy (time domain/frequency domain), the SQI representing the baseline drift (time domain/frequency domain), the SQI representing the high frequency noise (time domain/frequency domain), the SQI representing the signal purity (time domain/frequency domain), the SQI representing features of QRS complex (QRS complex energy ratio, amplitude ratio, etc.), and the SQI representing the differences/similarities between results detected by different algorithms.

At Step S220, the composite SQI is obtained of each physiological signal by calculating the obtained sub-SQI of each physiological signal, and applying the composite SQI of each physiological signal as the SQI in step S120.

Depending on the noise level, the composite SQI of signals could be categorized into five categories:

Category 4: the highest level of noise, where physiological signals cannot be distinguished by the human eye and cannot be analyzed by algorithms;

Category 3: a relatively high level of noise where physiological signals are difficult to be distinguished by the human eye and the algorithm analysis of physiological signals is totally affected;

Category 2: a general level of noise where physiological signals are easy to be distinguished by the human eye and the algorithm analysis of physiological signals is partially affected;

Category 1: a low level of noise, with slight noise and the algorithm analysis of physiological signals is not affected;

Category 0: the best signal quality where no noise could be distinguished by the human eye and the algorithm analysis of physiological signals is not affected at all;

The categorization of the composite SQI is not limited to the above five categories, which could be four or six categories. Moreover, the composite SQI could be based on the status of current signals, the categorization of signals, a combination, or a value calculated by certain mathematical method. The composite SQI could also be set to a high value when the signal quality is high, such as category 4, or a low value when the signal quality is low, such as category 0.

The composite SQI of EGG signal could be categorized according to the following criteria. The criteria are not limited to those shown below and could be any other criteria showing the degree of influence of the noise or the type of noise on algorithms:

Category 4: the worst signal quality, QRS complexes cannot be distinguished by the human eye and cannot be analyzed by algorithms at all;

Category 3: a relatively high level of noise, QRS complexes could be mainly distinguished by the human eye, but the algorithm analysis for detecting and categorizing QRS complexes is affected;

Category 2: a general level of noise, the algorithm analysis for categorizing QRS complexes is affected, but the algorithm analysis for detecting QRS complexes is not affected;

Category 1: a relatively low level of noise, the algorithm analysis for detecting and categorizing QRS complexes is not affected; and Category 0: the best signal quality, no noise could be distinguished by the human eye and the algorithm analysis is not affected at all;

Based on the above five sub-SQI, the composite SQI which evaluates physiological signals such as ECG signals, i.e., electrocardiosignal (named as ECGSQI for short in this embodiment) could be obtained by applying the following conditions (if one condition is not met, then the next condition is applied). Threshold values are set based on the following examples:

① kSQI correlation threshold: THD_K=7;
② bSQI correlation threshold: THD_B=80;
③ sSQI correlation threshold: THD_S=60;
④ hSQI correlation threshold: THD_H1=400; THD_H2=300; THD_H3=200; THD_H4=150;
⑤ bslSQI correlation threshold: THD_BSL1=40; THD_BSL2=20.

Condition 1: if (kSQI>THD_K) && (sSQI>THD_S||hSQI>THD_H1) && bslSQI>THD_BSL2, then ECGSQI=1;

Condition 2: if (kSQI>THD_K) && (sSQI>THD_S||hSQI>THD_H1) && bslSQI<=THD_BSL2, then ECGSQI=2;

Condition 3: if (bslSQI<=THD_BSL2) && (hSQI<=THD_H3), then ECGSQI=2;

Condition 4: if (bslSQI<=THD-BSL2) && (hSQI<=THD_H4), then ECGSQI=3;

Condition 5: if (THD_BSL2<bslSQI<=THD_BSL1) && (hSQI>THD_H2), then ECGSQI=1;

Condition 6: if (THD_BSL2<bslSQI<=THD_BSL1) && (THD_H3<hSQI<=THD_H2), then ECGSQI=2;

Condition 7: if (THD_BSL2<bslSQI<=THD_BSL1) && (hSQI<=THD_H3), then ECGSQI=3;

Condition 8: if (bslSQI>THD_BSL2) && (hSQI>THD_H4), then ECGSQI=0;

Condition 9: if (bslSQI>THD-BSL2) && (hSQI<=THD_H4), then ECGSQI=1;

Condition 10: if bSQI>THD-B, and ECGSQI>=3, then ECGSQI=2;

If none of the above conditions is met, then ECGSQI=0.

The calculation of the composite SQI is not limited to the above method. The key is to obtain the degree of influence or the effect of characteristics of the current signals on algorithm analysis. For example, in another embodiment, the calculation of the composite SQI is described as: when the sSQI, kSQI, hSQI, and bslSQI show high signal quality, to trust the result of bSQI and determine the composite SQI based on the bSQI; when the sSQI is low, the bSQI being distorted due to the interference of an abnormal spectral distribution, the composite SQI is obtained by taking threshold values of the kSQI, hSQI, and bslSQI; when the aforementioned conditions are not met and the kSQI shows that the signal quality is low, to decrease the level of trust in the signal quality by multiplying bSQI by an adjustment factor h. The detailed calculation and the setting of threshold values are shown as:

Threshold values are set as:
THD_K=7;
THD_B1=80, THD_B2=60, THD_B3=40, THD_B4=20;
THD_S=60;
THD_H1=300; THD_H2=200; THD_H3=150;
THD_BSL1=50; THD_BSL2=30; THD_BSL3=15.

Steps in the array of conditions are shown as below:

Condition 1: if (kSQI>=THD_K) && (sSQI>=THD_S) && (hSQI>=THD_H2) && (bslSQI>=THD_BSL2) is met, the composite SQI (named as ECGSQI) is categorized based on the bSQI as:

$$ECGSQI = \begin{cases} 4 & \text{if } bSQI < \text{THD\_B4} \\ 3 & \text{if } \text{THD\_B4} \le bSQI < \text{THD\_B3} \\ 2 & \text{if } \text{THD\_B3} \le bSQI < \text{THD\_B2} \\ 1 & \text{if } \text{THD\_B2} \le bSQI < \text{THD\_B1} \\ 0 & \text{if } \text{THD\_B1} \le bSQI \end{cases}$$

Condition 2: if condition 1 is not met, then condition 2 is: if (sSQI<THD_S), the composite SQI is obtained by taking threshold values of the kSQI, hSQI and bslSQI, $$ECGSQI = \begin{cases} 4 & \text{if } (kSQI < \text{THD\_K}) \,\&\&\, (hSQI < \text{THD\_H3}) \,\&\&\, (bslSQI < \text{THD\_BSL3}) \\ 3 & \text{if } (kSQI < \text{THD\_K}) \,\&\&\, (\text{THD\_H2} > hSQI >= \text{THD\_H3}) \,\&\&\, (\text{THD\_BSL2} > bslSQI >= \text{THD\_BSL3}) \\ 2 & \text{if } (kSQI < \text{THD\_K}) \,\&\&\, (\text{THD\_H1} > hSQI >= \text{THD\_H2}) \,\&\&\, (\text{THD\_BSL1} > bslSQI >= \text{THD\_BSL2}) \\ 1 & \text{if } (kSQI >= \text{THD\_K}) \,\&\&\, (hSQI >= \text{THD\_H1}) \,\&\&\, bslSQI >= \text{THD\_BSL1} \end{cases}$$

Condition 3: if condition 2 is not met, then condition 3 is: if (kSQI<THD_K), to decrease the level of trust in the signal quality by multiplying bSQI by an adjustment factor h, which is an empirical parameter adjusted based on experiments. In this embodiment, h=1.1.

$$ECGSQI = \begin{cases} 4 & \text{if } bSQI < THD_{B4} * h \\ 3 & \text{if } THD_{B4} * h <= bSQI < THD_{B3} * h \\ 2 & \text{if } THD\_B3 * h <= bSQI < THD\_B2 * h \\ 1 & \text{if } THD_{B2} * h <= bSQI < THD_{B1} * h \\ 0 & \text{if } THD_{B1} * h <= bSQI \end{cases}$$

Condition 4: if none of the above conditions is met, ECGSQI=0.

The calculation of the composite SQI of ECG is described above. For the calculation of the composite SQI of IPB and SPO2, the applied sub-SQI could be the SQI representing energy (time domain/frequency domain), such as the sSQI; the SQI representing the baseline drift (time domain/frequency domain), such as the bslSQI; the SQI representing the high frequency noise (time domain/frequency domain), such as the hSQI; the SQI representing the signal purity (time domain/frequency domain); the SQI representing features of QRS complex (QRS complex energy, amplitude, etc.). The composite SQI of IBP and SPO2 could be obtained via calculations similar to the method described above, but due to differences between their physiological signals and ECG signals, specific parameters in the calculation need to be adjusted.

Figure 3:
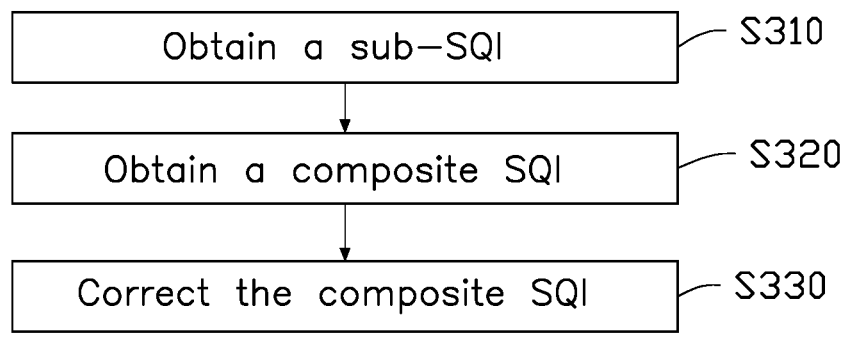
FIG. 3 is a flowchart illustrating another embodiment of the analysis of a physiological signal to obtain a signal quality index.

In the other embodiment shown in FIG. 3, for ECG signals, step S120, which obtains the SQI of each physiological signal by analyzing each of the at least two kinds of physiological signals via a processor of the monitoring device, could further include the following steps:

At Step S310, the sub-SQI characterizing the features or status of each physiological signal is obtained. This step could be the same as step S210 and the details are not here described.

At Step S320, the composite SQI of each physiological signal is obtained by calculating the obtained sub-SQI of each physiological signal. This step could be the same as step S220 and the details are not here described.

Figure 4:
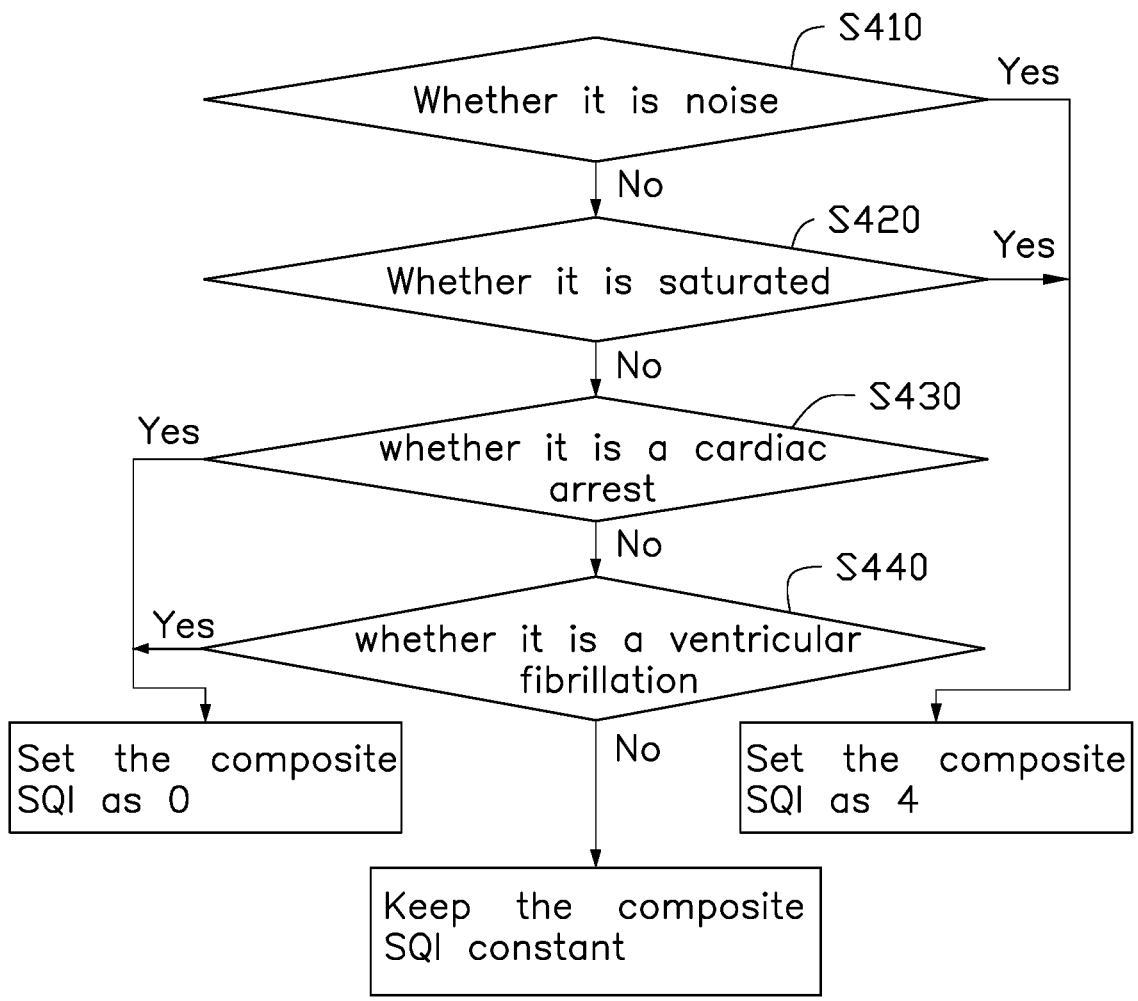
FIG. 4 is a flowchart illustrating corrections applied to a composite signal quality index.

At Step S330, the composite SQI of each physiological signal is corrected and the corrected composite SQI is set as the SQI of the physiological signal. As the composite SQI is not accurate in some circumstances, the approach to obtain the composite SQI needs to be corrected by pre-determinations, as shown in FIG. 4. The approach to correct the composite SQI includes the following steps:

At Step S410, a determination is made whether the signal is noise. If it is noise, then the composite SQI value is set as 4; if it is not noise, the method proceeds to the next condition. An example of deciding whether the signal is noise is given as follows kSQI correlation threshold: THD_K=7;
bSQI correlation threshold: THD_B=50;
sSQI correlation threshold: THD_S=50.

The determination of the level of noise could be based on the following two points: whether the detected pacing signal is greater than a predetermined noise value (for example, above 10) within a predetermined time (such as every per second); whether the high frequency noise of signals is greater than the threshold of noise determination. Whether the high frequency noise is too great could be determined by the previously calculated sub-SQI, or by the sign of high frequency noise obtained through some classical filtering methods or classical statistical methods, e.g., the number of times that the signal exceeded certain threshold within a time range (such as one second) as the sign. Choosing the previously calculated sub-SQI to do the determination may precede determining whether sSQI<THD_S and bSQI<THD_B and kSQI<THD_K. If these conditions are met, then the noise is considered as too great.

At Step S420, a determination is made whether the signal is saturated. If a sum of the time duration of the ECG data greater than a predetermined saturated threshold value in a time range (such as one second) for the current saturated determination exceed a saturated determination time threshold value (such as 0.5 second), and if no valid QRS complex is detected in the range of the saturated determining time threshold value, then the signal is considered to be saturated. Under the saturated condition, the composite SQI value is set as 4. If it is not saturated, then the method proceeds to the next condition.

At Step S430, a determination is made whether the signal is a cardiac arrest. If differences between the maximum and minimum value of the ECG signal in the current time range for determining cardiac arrest (such as 2 seconds) is smaller than the threshold of the arrest amplitude (such as 0.2 mV), or if no valid QRS complex is detected in the time range for determining cardiac arrest, then the signal is a cardiac arrest and the composite SQI is set as 0. If the signal is not a cardiac arrest, then the method proceeds to the next condition.

At Step S440, a determination is made whether it is a ventricular fibrillation (VF). If it is a VF, then the composite SQI is set as 0; if it is not a VF, then the composite SQI is not corrected. In this step, the determination of VF is based on the sub-SQI and morphological parameters of the waveform. The sub-SQI includes kSQI characterizing the type of VF and sSQI characterizing the ratio of the valid signals to the whole signals. Morphological parameters of the waveforms include whether it is a wide QRS complex (determined by the width of QRS complex, in this embodiment, if the width of QRS complex is greater than 140 ms, then consider it as a wide QRS complex), the ratio of the wide QRS complex in the time window, and differences between the maximum and minimum value of the waveform. To determine the VF, some threshold is first predetermined and then a determination is made based on these threshold values. For example, kSQI is a sub-SQI characterizing the type of VF with two threshold values. One is the extreme threshold THD_K1, when kSQI is smaller than this threshold it is highly probable to be VF; the other one is the typical threshold THD_K2, when the signal is smaller than this threshold, it is possible to be VF. Threshold THD_S of sSQI indicates that if the signal exceed this threshold then the current signal is less possible to be noise, while if the signal is below this threshold, then the current signal is possible to be noise. If the signal is higher than or equal to the extreme threshold of the ratio of wide QRS complex THD_WR1, then the current signal is probable to be VF. If the signal is higher than or equal to the typical threshold of the ratio of wide QRS complex THD_WR2, then the current signal is possible to be VF. If the signal is higher than the threshold of the number of wide QRS complex THD_WH, then the current signal is possible to be VF. If the signal is higher than the threshold of QRS complex number THD_Q, then the current signal is possible to be VF. Valid ECG signals are confirmed when the difference between the maximum and minimum value of the waveform is larger than the threshold of the signal difference THD_D.

An example is given to determine VF:

The threshold to determine VF is defined as following:

kSQI correlation threshold: THD_K1=7; THD_K2=4 sSQI correlation threshold: THD_S=60;

ratio of the wide QRS complex threshold: THD_WR1=0.6; THD_WR2=0.5;

the number of QRS complex threshold: THD_Q=3;

signal difference threshold: THD_D=0.2 mV.

Detailed steps to determine VF are listed as following:

Step A: determining the number of detected QRS complex in VF time window (VF index time window, such 4 seconds or 8 seconds)<=1, whether differences between the maximum and the minimum value of ECG signals in VF time window>THD_D, and whether kSQI<THD_K2. If all these three conditions are met, then it is determined to be VF. Otherwise, the method proceeds to the next step.

Step B: determining whether the QRS complex of the latest one second is the wide QRS complex. If the QRS complex of the latest one second is not the wide QRS complex, then it is not VF; if the QRS complex of the latest one second is the wide QRS complex, then the method proceeds to the next step.

Step C: determining whether the RR interval of QRS complex of the latest four seconds is inhomogeneous; if the ratio of wide QRS complex of QRS complex detected in the latest four seconds>THD_WR1 and the number of wide QRS complex>THD_WN; and if kSQI<=THD_K1. If all these three conditions are met, then it is determined to be VF. Otherwise the method proceeds to the next step. To determine that the RR interval is homogeneous, one of the following two conditions should be met. Condition 1: compare the RR interval of the current QRS complex to the RR intervals of the latest 16 QRS complex; if the difference between the current RR interval and more than half of the past RR intervals is smaller than 12.5%, then it is considered as homogeneous; Condition 2: If the difference between the current RR interval and the latest three past RR intervals is smaller than 12.5%, then it is considered as homogeneous.

Step D: If the RR interval of QRS complex detected in the latest four seconds is inhomogeneous; if kSQI<THD_K2 and sSQI>=THD_S. If these two conditions are both met, then it is determined to be VF. Otherwise, the method proceeds to the next step.

Step E: If the RR interval of QRS complex detected in the latest four seconds is inhomogeneous; if the detected ratio of wide QRS complex of QRS complex in the latest four seconds>THD_WR2 and the number of wide QRS complexes>THD_WN; and if kSQI<THD_K1 and sSQI>=THD_S. If all these conditions are met, then it is determined to be VF. Otherwise, the method proceeds to the next step.

Step F: If the RR interval of QRS complex detected in the latest four seconds is inhomogeneous; if kSQI<THD_K2 and sSQI>=THD_S; if the current detected number of QRS complex>=THD_Q. If all these conditions are met, then it is determined to be VF. Otherwise, it is determined to be not VF.

The pre-determination applied to correct the composite SQI is not limited to the approach shown in FIG. 4. An approach that improves the result of the composite SQI or directly assists the analysis of ECG results could be applied. Four conditions are provided in FIG. 4, and under these four conditions the methods mentioned above may result in wrong composite SQI, therefore corrections are needed. Different calculation methods of the composite SQI may lead to the calculation of the composite SQI that is not precise in other circumstances. Therefore, to obtain a more precise composite SQI, proper alternatives and modifications could be applied to FIG. 4. For example, only one or two or three conditions may be processed. The sequence of the conditions could also be modified, for example, such as first doing the saturation determination, and next doing the noise determination.

At Step S140, the fusion of the homologous physiological parameter values obtained from each of the at least two kinds of physiological signal based on the obtained SQI of each of the at least two kinds of physiological signal could be accomplished by various approaches. For example, the weighted average method could be applied to fuse the homologous physiological parameter values obtained from each physiological signal. The weighting of the homologous physiological parameter value obtained from each physiological signal is determined by the SQI of each physiological signal. The weighting of the homologous physiological parameter value obtained from each physiological signal could be obtained by a predetermined relation between the SQI and the weighting. A SQI indicating a good quality of the physiological signal has a higher weighting of the physiological parameter value than that of an indicated poor quality. Taking ECG IBP, SPO2 signals as examples, after obtaining the composite SQI of ECG and the heart rate value (HR), the composite SQI of IBP and the pulse rate value ($PR_{Ibp}$), and the composite SQI of SPO2 and the pulse rate value ($PR_{spo2}$), the weighting of ECG HR ($C_{ecg}$) could be calculated by the composite SQI of ECG the weighting of $PR_{Ibp}$ ($C_{ibp}$) could be calculated by the composite SQI of IBP, and the weighting of PRspo2 ($C_{spo2}$) could be calculated by the composite SQI of SPO2. Then, based on weightings and HR/pulse rate, the final fused heart rate value is calculated, wherein the predetermined relation between the SQI and the weighting is shown as below:

$$C = \begin{cases} 100 & SQI = 01 \\ 80 & SQI = 2 \\ 50 & SQI = 3 \\ 0 & SQI = 4 \end{cases}$$

The equation to calculate the final fused heart rate is defined as below:

$$HR = \frac{C_{ecg} * HR + C_{ibp} * PR_{ibp} + C_{spo2} * PR_{spo2}}{C_{ecg} + C_{ibp} + C_{spo2}} \quad \text{Equation 1}$$

If the obtained composite SQI calculated from the current ECG signal is 2 or 3, due to the interference of noise, the obtained HR may always be in a jumping status; while if the signal quality of the current IBP and SPO2 is good, the composite SQI is 0 or 1, the obtained PR calculated by IBP and SPO2 are both constant, in which case a relatively constant output value of HR could be obtained based on the equation of HR fusion. By this approach false alarms caused by the interference of ECG or HR jump (such as arrhythmia, tachycardia, etc.) could be successfully decreased, which enhances the anti-interference of the monitoring device and the accuracy of alarms. Moreover, it could make parameter data shown on the interface more stable, avoiding the operator distrust of the device.

Figure 5:
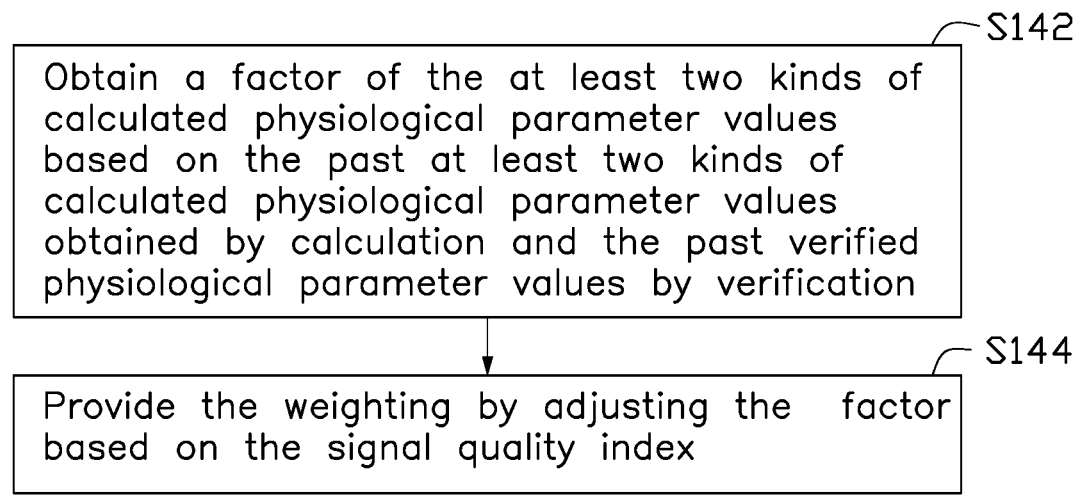
FIG. 5 is a schematic diagram illustrating a fusing process to obtain a weighting.

It should be understood, in addition to the predetermined relation between the SQI and the weighting, the weighting could also be obtained by other statistical methods, such as Kalman filtering method to fuse the at least two homologous physiological parameter values. For example, the weighting is obtained by the following steps as shown in FIG. 5:

At Step S142, a fusion factor of the homologous physiological parameter value is obtained from each physiological signal is determined based on past periods of the homologous physiological parameter values obtained from each physiological signal and verified physiological parameter values. Herein, homologous physiological parameter values can be assumed to be obtained from each physiological signal a, b, c at different past periods 1, 2, 3 are X1a, X1b, X1c, . . . ; X2a, X2b, X2c, . . . ; X3a, X3b, X3c, . . . , wherein the serial number 1, 2, 3 represent different past periods, and a, b, c represent different physiological signals. The verified past physiological parameter values (such as X1, X2, X3, wherein the serial number 1, 2, 3 represent the past period corresponding to each physiological parameter value) are correct physiological parameter values confirmed by experts. By certain mathematical methods, such as neural networks, Bayes (Bayesian) method, Kalman filtering, etc., the fusion factor Pa, Pb, Pc of homologous physiological parameter values could be determined by different physiological signals a, b, c. Thus:

$$Pa*X1a+Pb*X1b+Pc*X1c=X1;$$

$$Pa*X2a+Pb*X2b+Pc*X2c=X2;$$

$$Pa*X3a+Pb*X3b+Pc*X3c=X3.$$

At Step S144, weighting of homologous physiological parameter values obtained from each physiological signal is provided based on the SQI of each physiological signal and the obtained fusion factor of each homologous physiological parameter value. There are many approaches to determine the weighting of physiological parameter values depending on the representation of the SQI. For example, an index of the physiological parameter value Xa obtained from the physiological signal a is Pa, its SQI is SQIa (in this embodiment, a higher signal quality leads to a smaller SQI value), the weighting of the physiological parameter value Xa could be represented as: Ca=Pa/(SQIa+1)^2 or Ca=Pa/(SQIa+1). The equation for calculating the weighting Ca is not limited to the above two equations and could be adjusted based on the requirement. The basic principle of the equation is that the SQI indicating a good quality of the physiological signal has a higher weighting of the physiological parameter value than that of an indicated poor quality.

After obtaining the weighting by calculation, the fusion of physiological parameter values could proceed by the weighted average method similar to Equation 1.

To determine the weighting by physiological parameter values of past periods, the proportion of each physiological parameter value could be adjusted based on previous situations to make the fused value of the homologous physiological parameter values closer to the true situation.

Figure 6:
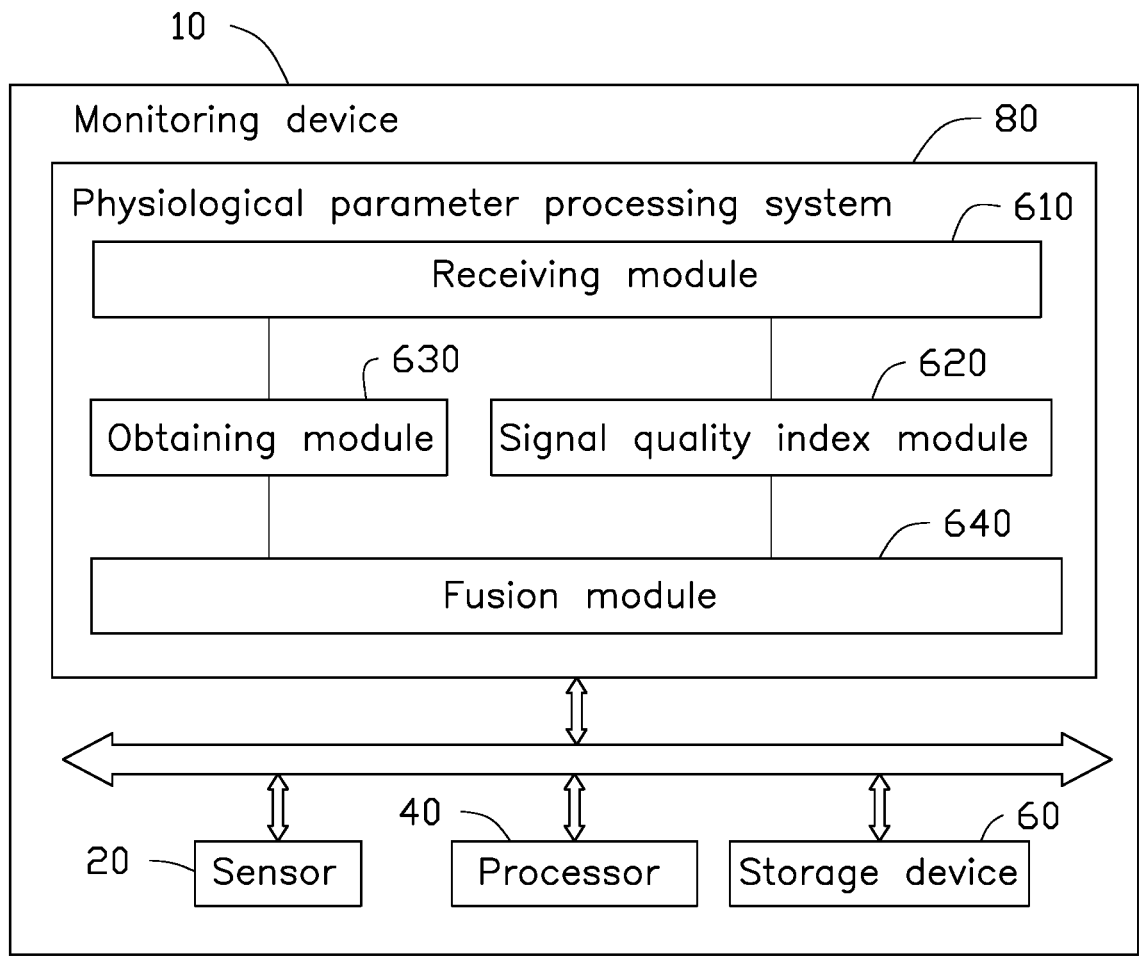
FIG. 6 is a schematic diagram of a monitoring device.
Figure 7:
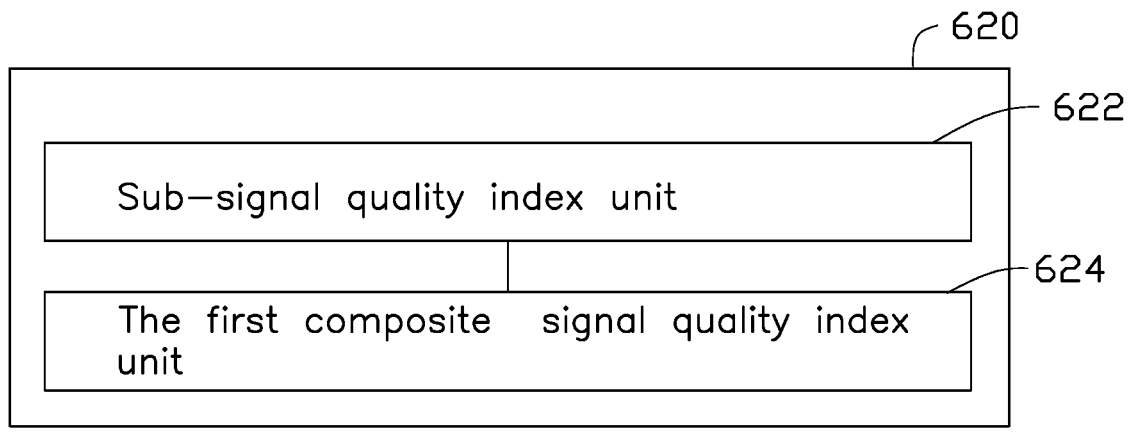
FIG. 7 is a schematic diagram of an embodiment of a signal quality index module.

The present disclosure also provide a physiological parameter processing system 80 for a monitoring device 10 which includes a sensor 20, a processor 40 and a storage device 60, shown in FIG. 6, including a receiving module 610, a signal quality index module 620, an obtaining module 630, and a fusion module 640.

The receiving module 610 acquires at least two kinds of physiological signals via the sensor 20 of the monitoring device 10. The physiological signal could be an electrocardiogram signal (ECG signal), an invasive blood pressure signal (IBP signal), or a blood oxygen signal (SPO2 signal). The phrase, "at least two kinds of physiological signals," may include only two signals and more than two signals. For example the number of physiological signals could be two, three, four, or more. The acquired physiological signals could be either original signals collected via the sensor or signals processed by a filter or other processing methods.

The signal quality index module 620 obtains a signal quality index (SQI) of each physiological signal by analyzing each of the at least two kinds of physiological signals. The SQI is an evaluation of the quality of signals. The SQI could be calculated by various approaches, such as an individual calculation or a comprehensive calculation. The SQI could also be corrected based on some pre-determinations. Approaches to obtain the SQI will be described in detail.

The obtaining module 630 obtains a homologous physiological parameter value corresponding to each of the at least two kinds of physiological signals by processing each of the at least two kinds of physiological signals. For example, a physiological parameter value may be obtained by IBP algorithm analysis, SPO2 algorithm analysis, and ECG algorithm analysis For example, diastolic pressure, systolic pressure, mean blood pressure and pulse rate could be obtained by processing the IBP signal, pulse rate and blood oxygen saturation degree could be obtained by processing the SPO2 signal, and heart rate and arrhythmia could be obtained by processing the ECG signal. Related to these physiological parameter values, the homologous physiological parameter values could be ECG heart rate (HR), IBP pulse rate ($PR_{Ibp}$) and SPO2 pulse rate (PRspo2). The homologous physiological parameter values indicate the same physiological status but are obtained from different signal sources.

The fusion module 640 fuses the homologous physiological parameter values based on the signal quality index of each of the at least two kinds of physiological signals and provides a fused value of the homologous physiological parameter values by the processor. The fusion could be applied by applying the weighted average method to fuse the at least two homologous physiological parameter values. A weighting of the physiological parameter value obtained from each physiological signal is determined by the SQI of each physiological signal. The SQI indicating a good quality of the physiological signal has a higher weighting of the physiological parameter value than that of an indicated poor quality. The fusing process could also proceed by other statistical methods, such as a Kalman filtering method, to fuse the homologous physiological parameter values obtained from each physiological signal.

The aforementioned physiological parameter processing system acquires at least two kinds of physiological signals and their respective SQIs and fuses the at least two homologous physiological parameter values based on the SQIs. Thus, the method can avoid the disadvantage of obtaining physiological parameters only based on one single physiological signal. A single physiological signal can be improved by use of the physiological parameter of the other physiology signal when the single physiological signal is interfered with.

Signal quality index module 620 includes a sub-signal quality index unit 622 and a first composite signal quality index unit 624.

The sub-signal quality index unit 622 obtains the sub-SQI characterizing features or status of each individual physiological signal. Taking ECG signal as an example, the sub-SQI could be one or more types of kSQI, bSQI, sSQI, hSQI, and bslSQI. The kSQI represents a type of ventricular fibrillation (VF) and is more likely to be noiseless QRS complex when kSQI has a higher value, generally a value of 7. The sSQI represents the ratio of the valid signal to the whole signal and is more likely to be noiseless QRS complex when sSQI has a higher value, generally a value of 0.6. The bslSQI represents the degree of baseline drift; a higher value of bslSQI indicates a smaller baseline drift which has less effect on the algorithm, it is therefore based on the effect which it has on the algorithm. The bslSQI could be divided into two levels or even more than two levels depending on the specific algorithm. The hSQI represents the magnitude of the high frequency noise; a higher value of hSQI indicates a lower high frequency noise which has less effect on the algorithm, therefore its effect on the algorithm hSQI could be divided into four levels or even more than four levels depending on the specific algorithm. The bSQI represents the magnitude of the composite noise; a smaller value of bSQI indicates a lower high frequency noise which has less effect on the algorithm, therefore its effect on the algorithm bSQI could be divided into fewer levels depending on the specific algorithm.

The kSQI could effectively represent the characteristic of the VF type, which is defined as:

$$kSQI = \frac{E\{(x-\mu_x)^4\}}{\sigma^4}$$

wherein, x is a discrete signal or a continuous series of signals, $\mu_x$ and $\sigma$ are the mean and the standard deviations of the discrete signal x or of the continuous series of signal x respectively, and E is a mathematical expectation operator.

The bSQI describes the percentage of matched beats by two QRS detection algorithms, representing the magnitude of noise, which is defined as follows:

$$bSQI = \frac{N_{matched}(k,w)}{N_{all}(k,w)} * 100$$

wherein, k is the QRS complex under analysis, w is a sliding analysis window (the width could be 10 seconds) centered in the analyzed QRS complex (k) with ½ window width at the left and right sides; $N_{matched}$ is the number of matches of the QRS complex in w detected by two different QRS detection algorithms (that is, any two types of QRS complex detection algorithms, for example DF algorithms and LT algorithms), and $N_{all}$ is the sum of the number of QRS complexes in w respectively detected by the two QRS detection algorithms. That is, $N_{all}=N_1+N_2-N_{matched}$, wherein $N_1$ is the number of QRS complexes in w detected by QRS detection algorithm 1, and $N_2$ is the number of QRS complexes in w detected by QRS detection algorithm 2. The matching of QRS complexes is based on the recommended standard from the Association for the Advancement of Medical Instrumentation (AAMI). When the labeled positions of QRS complexes detected by two algorithms are within 150 ms, these two QRS complexes are determined as being a single QRS complex. The meaning of bSQI is that the applied two algorithms could both label the QRS complexes correctly and a high bSQI value is obtained when the signal quality is good. The DF algorithm and LT algorithm could make different and misdetermined determinations and a low bSQI value is obtained when the interference happens. Thus, the bSQI could characterize the magnitude of noise. The calculation of the bSQI could also be applied to IBP and SPO2 while the matched time window should be determined according to own criteria of each, for example, 150 ms for the aforementioned ECG and 200 ms for IBP and SPO2.

The sSQI represents the ratio of the valid signals to the whole signals, showing the percentage of the power spectral density (PSD) of QRS complex in the total PSD, as shown below:

$$sSQI = 100 * \frac{\int_{f=thd1}^{f=thd2} PSD(k,w)df}{\int_{f=thd1}^{f=thd3} PSD(k,w)df}$$

Taking ECG as an example, most of the energy of QRS complex is focused on a frequency band centralized in 10 Hz with an approximate width of 10 Hz and the upper limit of the total energy is about 50 Hz. In the equation, thd1 could thus be selected as 5 Hz, thd2 could be selected as 14 Hz, and thd3 could be selected as 50 Hz. According to the spectral analysis of ECG signal, the energy of QRS complexes are focused on a frequency band centralized in 10 Hz with an approximate width of 10 Hz. The percentage of the PSD of the spectrum in the total PSD could be utilized as a reference index to determine the quality of ECG signal. The calculation of sSQI could also be applied to IBP and SPO2, but the bandwidth for the calculation should be determined according to the criteria of each, for example, calculating the ratio of 5-14 Hz to 5-5 Hz for the aforementioned ECG, while calculating the ratio of 0.2-12 Hz to 0.2-60 Hz for IBP and SPO2.

The hSQI is an index representing the magnitude of high frequency noise, calculated by:

hSQI=10+min($QRS_{i\_amplitude}$/hf_noise$_i$)

wherein $QRS_{i\_amplitude}$ refers to the amplitude of the currently detected QRS complex, hf_noise$_i$ is the mean value of the previous sum of 0.28 s–0.05 s before QRS complex, sum(i)=|hf(i)|+|hf(i−1)|+ . . . +|hf(i−5)|, wherein the hf is a value obtained by filtering ECG signal through a high pass filter: hf(i)=χ(i)−χ(i−1)+χ(i−2) wherein χ refers to the original waveform of ECG or the processed data of the waveform of ECG.

The bslSQI is an index representing the degree of baseline drift, calculated by:

bslSQI=10*min($QRS_{i\_amplitude}$/baseline$_{i\_amplitude}$)

$QRS_{i\_amplitude}$ is the difference between the maximum and minimum values in the range of QRS complex (R−0.07 s~R+0.08 s); baseline$_{i\_amplitude}$ is the difference between the maximum and minimum values of the window phase for the baseline determination (R−1 s~R+1 s).

The sub-SQI is not limited to the aforementioned five types. One classification or characterization of current signal could be the sub-SQI, such as the SQI representing energy (time domain/frequency domain), the SQI representing the baseline drift (time domain/frequency domain), the SQI representing the high frequency noise (time domain/frequency domain), the SQI representing the signal purity (time domain/frequency domain), the SQI representing features of QRS complex (QRS complex energy ratio, amplitude ratio, etc.), and the SQI representing the differences/similarities between results detected by different algorithms.

The first composite signal quality index unit 624 obtains the composite SQI of each physiological signal by calculating the obtained sub-SQI of each physiological signal and applying the composite SQI of each physiological signal as the SQI obtained by signal quality index module 620.

Depending on the noise level, the composite SQI of signals could be categorized into five categories:

Category 4: the highest level of noise, where physiological signals cannot be distinguished by the human eye and cannot be analyzed by algorithms;

Category 3: a relatively high level of noise where physiological signals are difficult to be distinguished by the human eye and the algorithm analysis of physiological signals is totally affected;

Category 2: a general level of noise where physiological signals are easy to be distinguished by the human eye and the algorithm analysis of physiological signals is partially affected;

Category 1: a low level of noise, with slight noise and the algorithm analysis of physiological signals is not affected;

Category 0: the best signal quality where no noise could be distinguished by the human eye and the algorithm analysis of physiological signals is not affected at all.

The categorization of the composite SQI is not limited to the above five categories, which could be four or six categories. Moreover, the composite SQI could be based on the status of current signals, the categorization of signals, a combination, or a value calculated by a certain mathematical method.

The composite SQI of an EGG signal could be categorized according to the following criteria. The criteria are not limited to those shown below and could be any other criteria showing the degree of influence of the noise or the type of noise on algorithms:

Category 4: the worst signal quality, QRS complexes cannot be distinguished by the human eye and cannot be analyzed by algorithms at all;

Category 3: a relatively high level of noise, QRS complexes could be mainly distinguished by the human eye, but the algorithm analysis for detecting and categorizing QRS complexes is affected;

Category 2: a general level of noise, the algorithm analysis for categorizing QRS complexes is affected, but the algorithm analysis for detecting QRS complexes is not affected;

Category 1: a relatively low level of noise, the algorithm analysis for detecting and categorizing QRS complexes is not affected;

Category 0: the best signal quality, no noise could be distinguished by the human eye and the algorithm analysis is not affected at all.

Based on the above five sub-SQI, the composite SQI which evaluates physiological signals such as ECG signals, i.e., electrocardiosignal (named as ECGSQI for short in this embodiment) could be obtained by applying the following conditions (if one condition is not met, then the next condition is applied). Threshold values are set based on the following examples:

① kSQI correlation threshold: THD_K=7;
② bSQI correlation threshold: THD_B=80;
③ sSQI correlation threshold: THD_S=60;
④ hSQI correlation threshold: THD_H1=400; THD_H2=300; THD_H3=200; THD_H4=150;
⑤ bslSQI correlation threshold: THD_BSL1=40; THD_BSL2=20.

Condition 1: if (kSQI>THD_K) && (sSQI>THD_S||hSQI>THD_H1) && bslSQI>THD_BSL2, then ECGSQI=1;

Condition 2: if (kSQI>THD_K) && (sSQI>THD_S||hSQI>THD_H1) && bslSQI<=THD_BSL2, then ECGSQI=2;

Condition 3: if (bslSQI<=THD_BSL2) && (hSQI<=THD_H3), then ECGSQI=2;

Condition 4: if (bslSQI<=THD-BSL2) && (hSQI<=THD_H4), then ECGSQI=3; Condition 5: if (THD_BSL2<bslSQI<=THD_BSL1) && (hSQI>THD_H2), then ECGSQI=1;

Condition 6: if (THD_BSL2<bslSQI<=THD_BSL1) && (THD_H3<hSQI<=THD_H2), then ECGSQI=2;

Condition 7: if (THD_BSL2<bslSQI<=THD_BSL1) && (hSQI<=THD_H3), then ECGSQI=3;

Condition 8: if (bslSQI>THD_BSL2) && (hSQI>THD_H4), then ECGSQI=0;

Condition 9: if (bslSQI>THD-BSL2) && (hSQI<=THD_H4), then ECGSQI=1; Condition 10: if bSQI>THD-B, and ECGSQI>=3, then ECGSQI=2;

If none of the above conditions is met, then ECGSQI=0.

The calculation of the composite SQI is not limited to the above method. The key is to obtain the degree of influence or the effect of characteristics of the current signals on algorithm analysis. For example, in another embodiment, the calculation of the composite SQI is described as: when the sSQI, kSQI, hSQI, and bslSQI show high signal quality, to trust the result of bSQI and determine the composite SQI based on the bSQI; when the sSQI is low, the bSQI is being distorted due to the interference of an abnormal spectral distribution, the composite SQI is obtained by taking threshold values of the kSQI, hSQI, and bslSQ1; when the aforementioned conditions are not met and the kSQI shows that the signal quality is low, to decrease the level of trust in the signal quality by multiplying bSQI by an adjustment factor h. The detailed calculation and the setting of threshold values are shown as:

Threshold values are set as:

THD_K=7;

THD_B1=80, THD_B2=60, THD_B3=40, THD_B4=20;

THD_S=60;

THD_H1=300; THD_H2=200; THD_H3=150;

THD_BSL1=50; THD_BSL2=30; THD_BSL3=15.

Steps in the array of conditions are shown as below:

Condition 1: if (kSQI>=THD_K) && (sSQI>=THD_S) && (hSQI>=THD_H2) && (bslSQI>=THD_BSL2) is met, the composite SQI (named as ECGSQI) is categorized based on the bSQI as:

$$ECGSQI = \begin{cases} 4 & \text{if } bSQI < \text{THD\_B4} \\ 3 & \text{if } \text{THD\_B4} \leq bSQI < \text{THD\_B3} \\ 2 & \text{if } \text{THD\_B3} \leq bSQI < \text{THD\_B2} \\ 1 & \text{if } \text{THD\_B2} \leq bSQI < \text{THD\_B1} \\ 0 & \text{if } \text{THD\_B1} \leq bSQI \end{cases}$$

Condition 2: if condition 1 is not met, then condition 2 is: if (sSQI<THD_S), the composite SQI is obtained by taking threshold values of the kSQI, hSQI and bslSQI, $$ECGSQI =  \begin{cases} 4 & \text{if } (kSQI < \text{THD\_K}) \,\&\&\, (hSQI < \text{THD\_H3}) \,\&\&\, (bslSQI < \text{THD\_BSL3}) \\ 3 & \text{if } (kSQI < \text{THD\_K}) \,\&\&\, (\text{THD\_H2} > hSQI >= \text{THD\_H3}) \,\&\&\, (\text{THD\_BSL2} > bslSQI >= \text{THD\_BSL3}) \\ 2 & \text{if } (kSQI < \text{THD\_K}) \,\&\&\, (\text{THD\_H1} > hSQI >= \text{THD\_H2}) \,\&\&\, (\text{THD\_BSL1} > bslSQI >= \text{THD\_BSL2}) \\ 1 & \text{if } (kSQI >= \text{THD\_K}) \,\&\&\, (hSQI >= \text{THD\_H1}) \,\&\&\, bslSQI >= \text{THD\_BSL1} \end{cases}$$

Condition 3: if condition 2 is not met, then condition 3 is: if (kSQI<THD_K), to decrease the level of trust in the signal quality by multiplying bSQI by an adjustment factor h, which is an empirical parameter adjusted based on experiments. In this embodiment, h=1.1.

$$ECGSQI = \begin{cases} 4 & \text{if } bSQI < THD_{B4} * h \\ 3 & \text{if } THD_{B4} * h <= bSQI < THD_{B3} * h \\ 2 & \text{if } \text{THD\_B3} * h <= bSQI < \text{THD\_B2} * h \\ 1 & \text{if } THD_{B2} * h <= bSQI < THD_{B1} * h \\ 0 & \text{if } THD_{B1} * h <= bSQI \end{cases}$$

Condition 4: if none of the above conditions is met, ECGSQI=0.

The calculation of the composite SQI of ECG is described above. For the calculation of the composite SQI of IPB and SPO2, the applied sub-SQI could be the SQI representing energy (time domain/frequency domain), such as the sSQI; the SQI representing the baseline drift (time domain/frequency domain), such as the bslSQI; the SQI representing the high frequency noise (time domain/frequency domain), such as the hSQI; the SQI representing the signal purity (time domain/frequency domain); the SQI representing features of QRS complex (QRS complex energy, amplitude, etc.). The composite SQI of IBP and SPO2 could be obtained via calculations similar to the method described above, but due to differences between their physiological signals and ECG signals, specific parameters in the calculation need to be adjusted.

Figure 8:
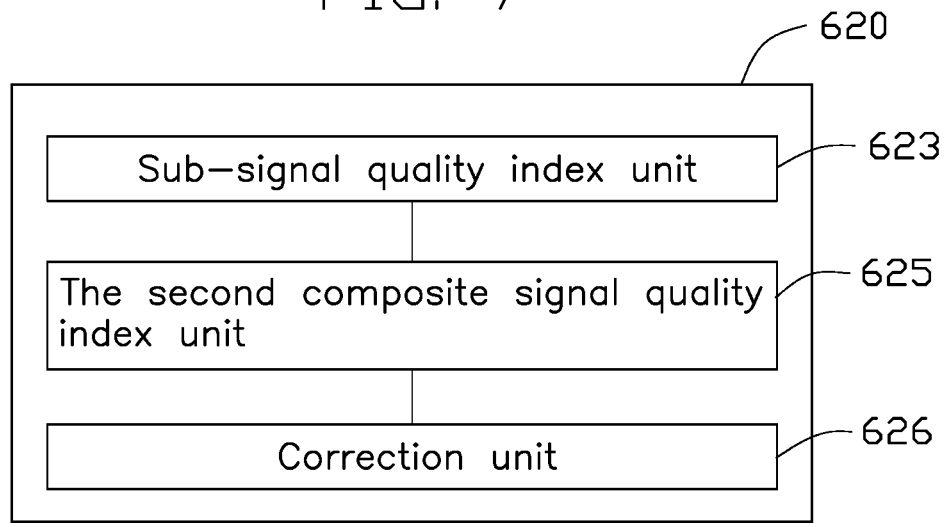
FIG. 8 is a schematic diagram of another embodiment of a signal quality index module.

In another embodiment as shown in FIG. 8, for ECG signals, signal quality index module 620 includes a sub-signal quality index unit 623, a second composite signal quality index unit 625 and a correction unit 626. Because the sub-signal quality index unit 623 and the second composite signal quality index unit 625 are similar to the sub-signal quality index unit 622 and the first composite signal quality index unit 624 in the aforementioned embodiment, the details are not here described.

The correction unit 626 corrects the composite SQI of each physiological signal and set the corrected composite SQI as the SQI of the physiological signal. As the composite SQI is not accurate in some circumstances, the approach to obtain the composite SQI needs to be corrected by pre-determinations, as shown in FIG. 4. The approach to correct the composite SQI includes the following steps:

At Step S410, a determination is made whether the signal is noise. If it is noise, then the composite SQI value is set as 4; if it is not noise, then the method proceeds to the next condition. An example to decide whether the signal is noise is given:

kSQI correlation threshold: THD_K=7;
bSQI correlation threshold: THD_B=50;
sSQI correlation threshold: THD_S=50.

The determination of the level of noise could be based on the following two points: whether the detected pacing signal is greater than a predetermined noise value (for example, above 10) within a predetermined time (such as every per second); and whether the high frequency noise of signals is greater than the threshold of noise determination. Whether the high frequency noise is too great could be determined by the previously calculated sub-SQI, or by the sign of high frequency noise obtained through some classical filtering methods, or some classical statistical methods, e.g., the number of times that the signal exceeded certain threshold within a time range (such as one second) as the sign. Choosing the previously calculated sub-SQI to do the determination, a determination is made whether sSQI<THD_S and bSQI<THD_B and kSQI<THD_K. If these conditions are met, then the noise is considered as too great.

At Step S420, a determination is made whether the signal is saturated. If a sum of the time duration of the ECG data greater than a predetermined saturated threshold value in a time range (such as one second) for the current saturated determination exceed a saturated determination time threshold value (such as 0.5 second), and if no valid QRS complex is detected in the range of the saturated determining time threshold value, then the signal is considered as saturated. Under the saturated condition, the composite SQI value is set as 4. If it is not saturated, the method proceeds to the next condition.

At Step S430, a determination is made whether the signal is a cardiac arrest. If differences between the maximum and minimum value of the ECG signal in the current time range for determining cardiac arrest (such as 2 seconds) is smaller than the threshold of the arrest amplitude (such as 0.2 mV), or if no valid QRS complex is detected in the time range for determining cardiac arrest, then the signal is a cardiac arrest and the composite SQI is set as 0. If the signal is not a cardiac arrest, then the method proceeds to the next condition.

At Step S440, a determination is made whether it is a ventricular fibrillation (VF). If it is a VF, then the composite SQI is set as 0; if it is not a VF, then the composite SQI is not corrected. In this step, the determination of VF is based on the sub-SQI and morphological parameters of the waveform. The sub-SQI includes: kSQI characterizing the type of VF and sSQI characterizing the ratio of the valid signals to the whole signals. Morphological parameters of the waveforms include: whether it is a wide QRS complex (determined by the width of QRS complex, in this embodiment, if the width of QRS complex is greater than 140 ms, then consider it as a wide QRS complex), the ratio of wide QRS complex in the time window, differences between the maximum and minimum value of the waveform. To determine the VF, some threshold is first predetermined and then a determination is made based on these threshold values. For example, kSQI is a sub-SQI characterizing the type of VF with two threshold values: one is the extreme threshold THD_K1, when kSQI is smaller than this threshold it is highly probable to be VF; the other one is the typical threshold THD_K2, when the signal is smaller than this threshold, it is possible to be VF. Threshold THD_S of sSQI indicates that if the signal exceed this threshold then the current signal is less possible to be noise, while if the signal is below this threshold then the current signal is possible to be noise. If the signal is higher than or equal to the extreme threshold of the ratio of wide QRS complex THD_WR1, then the current signal is probable to be VF. If the signal is higher than or equal to the typical threshold of the ratio of wide QRS complex THD_WR2, then the current signal is possible to be VF. If the signal is higher than the threshold of the number of wide QRS complex THD_WH, then the current signal is possible to be VF. If the signal is higher than the threshold of QRS complex number THD_Q, then the current signal is possible to be VF. Valid ECG signals are confirmed when the difference between the maximum and minimum value of the waveform is larger than the threshold of the signal difference THD_D.

An example is given to determine VF:

The threshold to determine VF is defined as following:

kSQI correlation threshold: THD_K1=7; THD_K2=4 sSQI correlation threshold: THD_S=60;

ratio of the wide QRS complex threshold: THD_WR1=0.6; THD_WR2=0.5;

the number of QRS complex threshold: THD_Q=3;

signal difference threshold: THD_D=0.2 mV.

Detailed steps to determine VF are listed as following:

Step A: determining the number of detected QRS complex in VF time window (VF index time window, such 4 seconds or 8 seconds)<=1, whether differences between the maximum and the minimum value of ECG signals in VF time window>THD_D, and whether kSQI<THD_K2. If all these three conditions are met, then it is determined to be VF. Otherwise, the method proceeds to the next step.

Step B: determining whether the QRS complex of the latest one second is the wide QRS complex. If the QRS complex of the latest one second is not the wide QRS complex, then it is not VF; if the QRS complex of the latest one second is the wide QRS complex, then the method proceeds to the next step.

Step C: determining whether the RR interval of QRS complex of the latest four seconds is inhomogeneous; if the ratio of wide QRS complex of QRS complex detected in the latest four seconds>THD_WR1 and the number of wide QRS complex>THD_WN; and if kSQI<=THD_K1. If all these three conditions are met, then it is determined to be VF. Otherwise the method proceeds to the next step. To determine the RR interval as homogeneous, one of the following two conditions should be met. Condition 1: the RR interval of the current QRS complex is compared to the RR intervals of the latest 16 QRS complex; if the difference between the current RR interval and more than half of the past RR intervals is smaller than 12.5%, then it is considered as homogeneous. Condition 2: If the difference between the current RR interval and the latest three past RR intervals is smaller than 12.5%, then it is considered as homogeneous.

Step D: If the RR interval of QRS complex detected in the latest four seconds is inhomogeneous; if kSQI<THD_K2 and sSQI>=THD_S. If these two conditions are both met, then it is determined to be VF. Otherwise, the method proceed to the next step.

Step E: If the RR interval of QRS complex detected in the latest four seconds is inhomogeneous; if the detected ratio of wide QRS complex of QRS complex in the latest four seconds>THD_WR2 and the number of wide QRS complexes>THD_WN; and if kSQI<THD_K1 and sSQI>=THD_S. If all these conditions are met, then it is determined to be VF. Otherwise, the method proceeds to the next step.

Step F: If the RR interval of QRS complex detected in the latest four seconds is inhomogeneous; if kSQI<THD_K2 and sSQI>=THD_S; if the current detected number of QRS complex>=THD_Q. If all these conditions are met, then it is determined to be VF. Otherwise, it is determined to be not VF.

The pre-determination applied to correct the composite SQI is not limited to the approach shown in FIG. 4. An approach that improves the result of the composite SQI or directly assists the analysis of ECG results could be applied. Four conditions are provided in FIG. 4, and under these four conditions the methods mentioned above may result in a wrong composite SQI; therefore corrections are needed. Different calculation methods of the composite SQI may lead to a calculation of the composite SQI that is not precise in other circumstances. Therefore, to obtain a more precise composite SQI, proper alternatives and modifications could be applied to FIG. 4. For example, only one or two or three conditions may be processed. The sequence of the conditions could also be modified, for example, first doing the saturation determination, and next doing the noise determination.

The fusion module 640, which fuses the homologous physiological parameter values obtained from each physiological signal based on the obtained SQI of each of the at least two kinds of physiological signals, could be accomplished by various approaches. For example, the weighted average method could be applied to fuse the homologous physiological parameter values obtained from each physiological signal. The weighting of the homologous physiological parameter value obtained from each physiological signal is determined by the SQI of each physiological signal. The weighting of the homologous physiological parameter value obtained from each physiological signal could be obtained by a predetermined relation between the SQI and the weighting. The SQI indicating a good quality of the physiological signal has a higher weighting of the physiological parameter value than that of an indicated poor quality. Take ECG IBP, SPO2 signals as examples. After obtaining the composite SQI of ECG and the heart rate value (HR), the composite SQI of IBP and the pulse rate value ($PR_{Ibp}$), and the composite SQI of SPO2 and the pulse rate value ($PR_{spo2}$), the weighting of ECG HR ($C_{ecg}$) could be calculated by the composite SQI of ECG the weighting of PRIbp ($C_{ibp}$) could be calculated by the composite SQI of IBP, and the weighting of PRspo2 ($C_{spo2}$) could be calculated by the composite SQI of SPO2. Then, based on weightings and HR/pulse rate, the final fused heart rate value is calculated, wherein the predetermined relation between the SQI and the weighting is shown as below:

$$C = \begin{cases} 100 & SQI = 01 \\ 80 & SQI = 2 \\ 50 & SQI = 3 \\ 0 & SQI = 4 \end{cases}$$

The equation to calculate the final fused heart rate is defined as below:

$$HR = \frac{C_{ecg} * HR + C_{ibp} * PR_{ibp} + C_{spo2} * PR_{spo2}}{C_{ecg} + C_{ibp} + C_{spo2}} \quad \text{Equation 1}$$

If the obtained composite SQI calculated from the current ECG signal is 2 or 3, due to the interference of noise the obtained HR may always be in a jumping status; while if the signal quality of the current IBP and SPO2 is good, the composite SQI is 0 or 1, the obtained PR calculated by IBP and SPO2 are both constant, a relative constant output value of HR could be obtained based on the equation of HR fusion. By this approach false alarms caused by the interference of ECG or HR jump (such as arrhythmia, tachycardia, etc.) could be successfully decreased, which enhances the anti-interference of the monitoring device and the accuracy of alarms.

Figure 9:
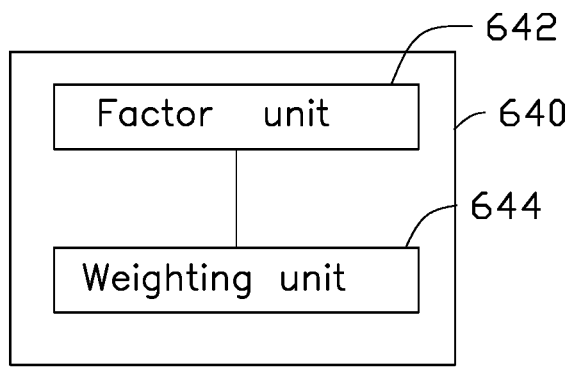
FIG. 9 is a schematic diagram of a fusing module.

In addition to the predetermined relation between the SQI and the weighting, the weighting could also be obtained by other statistical methods, such as a Kalman filtering method, to fuse the at least two homologous physiological parameter values. For example, as shown in FIG. 9, the fusion module 640 includes a factor unit 642 and a weighting unit 644. The weighting is obtained by the following approach:

The factor unit 642 obtains a fusion factor of the homologous physiological parameter value from each physiological signal, which is determined based on past periods of the homologous physiological parameter value obtained from each physiological signal and verified physiological parameter values. Herein, assume homologous physiological parameter values obtained from each physiological signal a, b, c at different past periods 1, 2, 3 are X1a, X1b, X1c, . . . ; X2a, X2b, X2c, . . . ; X3a, X3b, X3c, . . . , wherein the serial number 1, 2, 3 represent different past periods, a, b, c represent different physiological signals. The verified past physiological parameter values (such as X1, X2, X3, wherein the serial number 1, 2, 3 represent the past period corresponding to each physiological parameter value) are correct physiological parameter values confirmed by experts. By certain mathematical methods, such as neural networks, Bayes (Bayesian) method, Kalman filtering, etc., the fusion factor Pa, Pb, Pc of homologous physiological parameter values could be determined by different physiological signals a, b, c. Thus:

$$Pa*X1a+Pb*X1b+Pc*X1c=X1;$$

$$Pa*X2a+Pb*X2b+Pc*X2c=X2;$$

$$Pa*X3a+Pb*X3b+Pc*X3c=X3.$$

The weighting unit 144 provides the weighting of homologous physiological parameter values obtained from each physiological signal based on the SQI of each physiological signal and the obtained fusion factor of each homologous physiological parameter value. There are many approaches to determine the weighting of physiological parameter values depending on the representation of the SQI. For example, the index of the physiological parameter value Xa obtained from the physiological signal a is Pa, its SQI is SQIa (in this embodiment, a higher signal quality leads to a smaller SQI value), the weighting of the physiological parameter value Xa could be represented as: $Ca=Pa/(SQIa+1)^2$ or $Ca=Pa/(SQIa+1)$. The equation for calculating the weighting Ca is not limited to the above two equations and could be adjusted based on the requirement. The basic principle of the equation is that the SQI indicating a good quality of the physiological signal has a higher weighting of the physiological parameter value than that of an indicated poor quality.

After obtaining the weighting by calculation, the fusion of physiological parameter values could proceed by the weighted average method similar to Equation 1.

To determine the weighting with physiological parameter values of past periods, the proportion of each physiological parameter value is adjusted based on previous situations to make the fused value of the homologous physiological parameter values closer to the true situation.

The disclosed physiological parameter processing method and system can be applied to monitoring devices which includes a sensor, a processor and a storage device. The embodiments mentioned above only specifically describe a few embodiments of the present disclosure in detail, which should not be understood as a limitation to the scope of the present disclosure. It should be noted that, for one of the ordinary skill in the art, variations and improvements could be made based on the present disclosure, which belongs to the scope of the present disclosure.

What is claimed is:

1. A method executed by a processor of a monitoring device, comprising:
    acquiring, by the processor, from at least two different sensors, at least two signals indicating a same physiological parameter;
    for each of the signals, obtaining, by the processor, a respective signal quality index corresponding to the signal;
    for each of the signals, obtaining, by the processor, a respective physiological parameter value corresponding to the signal;
    for each of the signals, determining, by the processor, a weighting of the respective physiological parameter value corresponding to the signal based on the signal quality index corresponding to the signal and a predetermined relationship between signal quality indexes and weightings, the signal quality index indicating a good quality of the physiological signal having a higher weighting of the physiological parameter value, while the signal quality index indicating a poor quality of the physiological signal has a lower weighting of the physiological parameter value;
    fusing, by the processor, the physiological parameter values based on the signal quality index of each of the signals and the weighting of the physiological parameter value of each of the signals; and
    providing a fused value of the physiological parameter values.

2. The method of claim 1, wherein the weighting of the physiological parameter value obtained from each of the signals is based on a fusion factor, wherein the fusion factor is determined from past physiological parameter values and verified physiological parameter values.

3. The method of claim 1, wherein the signal quality index of each of the signals is obtained by:
    obtaining at least two sub-signal quality indexes of each of the signals, the at least two sub-signal quality indexes characterizing different features or status of each of the signals; and
    calculating a composite signal quality index of each of the signals based on the at least two sub-signal quality indexes of each of the signals.

4. The method of claim 3, wherein the at least two sub-signal quality indexes characterize at least two of an energy value, signal purity, a feature of a QRS complex, a type of ventricular fibrillation, a ratio of valid signal to whole signal, baseline drift, high frequency noise, and a noise value.

5. The method of claim 1, wherein the signal quality index of each of the signals is obtained by:

obtaining a sub-signal quality index characterizing features or status of each of the signals;
calculating a composite signal quality index of each of the signals based on the sub-signal quality index of each of the signals.

6. A physiological parameter processing system comprising:
a monitoring device including a processor;
a storage device storing program instructions;
a plurality of different sensors configured to acquire at least two signals that indicate a same physiological parameter;
wherein the processor is configured to execute the program instructions stored in the storage device, the program instructions being configured to, for each of the signals, obtain a respective signal quality index corresponding to the signal; for each of the signals, obtain a respective physiological parameter value corresponding to the signal; for each of the signals, determine a weighting of the respective physiological parameter value corresponding to the signal based on the signal quality index corresponding to the signal and a predetermined relationship between signal quality indexes and weightings, the signal quality index indicating a good quality of the physiological signal having a higher weighting of the physiological parameter value, while the signal quality index indicating a poor quality of the physiological signal has a lower weighting of the physiological parameter value; fuse physiological parameter values based on the signal quality index of each of the signals and the weighting of the physiological parameter value of each of the signals;
and provide a fused value of the physiological parameter values.

7. The system of claim 6, wherein the weighting of the physiological parameter value obtained from each of the signals is based on a fusion factor, wherein the fusion factor is determined from past physiological parameter values and verified physiological parameter values.

8. The system of claim 6, wherein the instructions are configured to obtain a signal quality index of each of the signals by:
obtaining at least two sub-signal quality indexes of each of the signals, the at least two sub-signal quality indexes characterizing different features or status of each of the signals; and
calculating a composite of the at least two sub-signal quality indexes of each of the signals.

9. The system of claim 8, wherein the at least two sub-signal quality indexes characterize at least two of an energy value, a signal purity, a feature of a QRS complex, a type of ventricular fibrillation, a ratio of valid signal to whole signal, a baseline drift, high frequency noise, and a noise value.

10. A monitoring device comprising:
a plurality of different sensors configured to acquire at least two signals that indicate a same physiological parameter,
a storage device storing program instructions; and
at least one processor configured to execute the program instructions, wherein the program instructions are configured to:
for each of the signals, obtain a respective signal quality index corresponding to the signal;
for each of the signals, obtain a respective physiological parameter value corresponding to the signal;
for each of the signals, determine a weighting of the respective physiological parameter value corresponding to the signal based on the signal quality index corresponding to the signal and a predetermined relationship between signal quality indexes and weightings, the signal quality index indicating a good quality of the physiological signal having a higher weighting of the physiological parameter value, while the signal quality index indicating a poor quality of the physiological signal has a lower weighting of the physiological parameter value;
fuse the physiological parameter values based on the signal quality index of each of the signals and the weighting of the physiological parameter value of each of the signals; and
provide a fused value of the physiological parameter values.

11. The device of claim 10, wherein the weighting of the physiological parameter value obtained from each of the signals is based on a fusion factor, wherein the fusion factor is determined from past physiological parameter values and verified physiological parameter values.

12. The device of claim 10, wherein the signal quality index of each of the signals is obtained by:
obtaining at least two sub-signal quality indexes of each of the signals, the at least two sub-signal quality indexes characterizing different features or status of each of the signals; and
calculating a composite of the at least two sub-signal quality indexes of each of the signals.

13. The device of claim 12, wherein the at least two sub-signal quality indexes characterize at least one of an energy value, a signal purity, a feature of a QRS complex, a type of ventricular fibrillation, a ratio of valid signal to whole signal, a baseline drift, high frequency noise, and a noise value.

14. The device of claim 10, wherein the same physiological parameter comprises heart rate, and wherein the at least two signals are selected from the group consisting of an invasive blood pressure signal, a blood oxygen signal, and an electrocardiogram (ECG) signal.

* * * * *